United States Patent
Nomura et al.

(10) Patent No.: US 9,309,264 B2
(45) Date of Patent: Apr. 12, 2016

(54) METHOD FOR ADSORBING CARBON DIOXIDE ONTO POROUS METAL-ORGANIC FRAMEWORK MATERIALS, METHOD FOR COOLING POROUS METAL-ORGANIC FRAMEWORK MATERIALS, METHOD FOR OBTAINING ALDEHYDE USING POROUS METAL-ORGANIC FRAMEWORK MATERIALS, AND METHOD FOR WARMING POROUS METAL-ORGANIC FRAMEWORK MATERIALS

(71) Applicant: Panasonic Corporation, Osaka (JP)

(72) Inventors: Takaiki Nomura, Osaka (JP); Takashi Kouzaki, Osaka (JP); Takahiro Kurabuchi, Osaka (JP); Kazuhito Hato, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 89 days.

(21) Appl. No.: 14/476,739

(22) Filed: Sep. 4, 2014

(65) Prior Publication Data

US 2015/0073164 A1   Mar. 12, 2015

(30) Foreign Application Priority Data

Sep. 12, 2013 (JP) .................. 2013-189188
Sep. 12, 2013 (JP) .................. 2013-189189

(51) Int. Cl.
*C07F 1/08* (2006.01)
*B01J 20/22* (2006.01)
(Continued)

(52) U.S. Cl.
CPC .............. *C07F 1/08* (2013.01); *B01D 53/323* (2013.01); *B01J 20/226* (2013.01);
(Continued)

(58) Field of Classification Search
CPC ........... C07F 1/08; C07F 11/00; C07C 45/38; C07C 51/412; C07C 47/02; C07C 63/307; C07C 63/24; B01J 31/1691; B01J 20/3425; B01J 20/3441; B01J 20/226; B01D 53/323
USPC ........ 556/115; 568/420; 423/352, 483, 437.1, 423/580.1

See application file for complete search history.

(56) References Cited

U.S. PATENT DOCUMENTS 7,902,535 B2   3/2011   Matsui et al.
8,115,024 B2   2/2012   Schubert et al.
(Continued)

FOREIGN PATENT DOCUMENTS

JP   2000-178279   6/2000
JP   2000-202283   7/2000
(Continued)

*Primary Examiner* — Porfirio Nazario Gonzalez
(74) *Attorney, Agent, or Firm* — McDermott Will & Emery LLP

(57) ABSTRACT

The present invention provides a method for adsorbing carbon dioxide onto porous metal-organic framework materials, a method for cooling porous metal-organic framework materials, a method for obtaining aldehyde using porous metal-organic framework materials and a method for warming porous metal-organic framework materials. In each method, porous metal-organic framework materials are used while an electric field or an electromagnetic field is applied to the porous metal-organic framework materials, or while a magnetic field or an electromagnetic field is applied to the porous metal-organic framework materials. If an electric field is applied, at least one organic compound included in the porous metal-organic framework materials is a polar compound. Instead, if a magnetic field is applied, at least one metal included in the porous metal-organic framework materials has an unpaired electron.

30 Claims, 9 Drawing Sheets

(51) Int. Cl.
*C07C 63/24* (2006.01)
*B01J 20/34* (2006.01)
*B01J 31/16* (2006.01)
*C07C 63/307* (2006.01)
*B01D 53/32* (2006.01)
*F17C 11/00* (2006.01)
*C07C 47/02* (2006.01)
*C07C 45/38* (2006.01)
*C07C 51/41* (2006.01)
*B01J 23/72* (2006.01)

(52) U.S. Cl.
CPC ......... *B01J 20/3425* (2013.01); *B01J 20/3441* (2013.01); *B01J 23/72* (2013.01); *B01J 31/1691* (2013.01); *C07C 45/38* (2013.01); *C07C 47/02* (2013.01); *C07C 51/412* (2013.01); *C07C 63/24* (2013.01); *C07C 63/307* (2013.01); *F17C 11/00* (2013.01); *B01D 2253/204* (2013.01); *B01D 2257/504* (2013.01); *B01J 2231/763* (2013.01); *B01J 2531/16* (2013.01)

(56) References Cited

U.S. PATENT DOCUMENTS

| | | |
|---|---|---|
| 2009/0042000 A1 | 2/2009 | Schubert et al. |
| 2010/0076220 A1 | 3/2010 | Schubert et al. |
| 2010/0126344 A1 | 5/2010 | Stein et al. |
| 2012/0091064 A1 | 4/2012 | Schubert et al. |

FOREIGN PATENT DOCUMENTS

| | | |
|---|---|---|
| JP | 2002-276898 | 9/2002 |
| JP | 2004-196594 | 7/2004 |
| JP | 2005-097530 | 4/2005 |
| JP | 2005-228773 | 8/2005 |
| JP | 2005-329317 | 12/2005 |
| JP | 2006-000617 | 1/2006 |
| JP | 2006-248989 | 9/2006 |
| JP | 2009-526011 | 7/2009 |
| JP | 2010-142679 | 7/2010 |
| JP | 2010-523308 | 7/2010 |
| JP | 2012-228667 | 11/2012 |
| WO | 2012/119069 A2 | 9/2012 |

METHOD FOR ADSORBING CARBON DIOXIDE ONTO POROUS METAL-ORGANIC FRAMEWORK MATERIALS, METHOD FOR COOLING POROUS METAL-ORGANIC FRAMEWORK MATERIALS, METHOD FOR OBTAINING ALDEHYDE USING POROUS METAL-ORGANIC FRAMEWORK MATERIALS, AND METHOD FOR WARMING POROUS METAL-ORGANIC FRAMEWORK MATERIALS

BACKGROUND

1. Field of the Invention

The present invention relates to a method for adsorbing carbon dioxide onto porous metal-organic framework materials, a method for cooling porous metal-organic framework materials, a method for obtaining aldehyde using porous metal-organic framework materials and a method for warming porous metal-organic framework materials.

2. Description of the Related Art

U.S. Pat. No. 8,115,024 discloses porous metal-organic framework materials. As is disclosed in U.S. Pat. No. 8,115,024, porous metal-organic framework materials can be an alternative to inorganic zeolites for the most varied applications. Such applications are, for example, in the field of storage, separation or controlled release of chemical substances, such as for example, gases, or in the field of catalysis.

Porous metal-organic framework materials typically comprise at least one, at least bidentate, organic compound bound by coordination to at least one metal ion. Examples of porous metal-organic framework materials are copper—organic framework materials. U.S. Pat. No. 8,115,024 discloses Cu—organic framework materials in which the metal is copper (II) ion and the organic compound is 1,3,5-benzene tricarboxylic acid.

SUMMARY

The present invention provides a method for cooling porous metal-organic framework materials, the method comprising:

(a) applying an electric field or an electromagnetic field to the porous metal-organic framework materials containing an adsorbate such that the adsorbate is released from the porous metal-organic framework materials, wherein the porous metal-organic framework materials contain
at least one metal ion, and
at least one organic compound bound by coordination bond to the at least one metal ion; and
the at least one organic compound is a polar compound.

The present invention provides a method for cooling porous metal-organic framework materials, the method comprising:

(a) applying a magnetic field or an electromagnetic field to the porous metal-organic framework materials containing an adsorbate such that the adsorbate is released from the porous metal-organic framework materials, wherein the porous metal-organic framework materials contain
at least one metal ion, and
at least one organic compound bound by coordination bond to the at least one metal ion; and
the at least one metal ion has an unpaired electron.

Regarding the spirit of the present invention, see the "conclusion" paragraph described at the end of the present specification.

The present invention provides a method for adsorbing carbon dioxide onto porous metal-organic framework materials more effectively, a method for cooling porous metal-organic framework materials more effectively, a method for obtaining aldehyde using porous metal-organic framework materials and a method for warming porous metal-organic framework materials more effectively.

DETAILED DESCRIPTION OF THE EMBODIMENTS

The present invention will be described below in more detail.

(1. Porous Metal-Organic Framework Materials)

First, porous metal-organic framework materials will be described. Porous metal-organic framework materials are well known. A method for preparing porous metal framework materials is also well known.

As is disclosed in U.S. Pat. No. 8,115,024, porous metal-organic framework materials contain at least one metal ion and at least one organic compound. The at least one organic compound is bound by coordination to the at least one metal ion. The at least one organic compound is at least bidentate.

An example of the at least one metal ion is a metal ion selected from the elements of groups II-XIII of the Periodic table of the Elements. An example of the desirable metal ion is $Ti^{3+}$, $Cr^{3+}$, $Mn^{2+}$, $Fe^{3+}$, $Co^{2+}$, $Ni^{2+}$, or $Cu^{2+}$. $Cu^{2+}$ is more desirable. Two or more kinds of the metal ions may be used. When a magnetic field is applied to the porous metal-organic framework materials, note that the at least one metal ion must not be $Zn^{2+}$, $Cd^{2+}$ or $Hg^{2+}$. This will be described later in more detail.

The at least one organic compound has at least one functional group which is capable of forming at least two coordination bonds to the at least one metal ion.

An example of the functional group which is capable of forming the coordination bond is —COOH, —CN, —$NR_3R_4$, or —Z (Z represents halogen such as —Cl.) Each of $R_3$ and $R_4$ independently represents a hydrocarbon group which can be substituted with a substituent.

An example of the at least one organic compound is:
$R_1(COOH)_n$, or
$R_2(N\text{—}R_3R_4)_n$
where
n represents an integer of two or more, and
each $R_1$, $R_2$, $R_3$, and $R_4$ independently represents a hydrocarbon group which can be substituted with a substituent.

The at least one organic compound may have a functional group X which is not bound by coordination to the metal ion, as long as the at least one organic compound has the at least one functional group which is capable of forming at least two coordination bonds to the at least one metal ion.

An example of such an organic compound is:
$R_5X_m(COON)_n$, or
$R_6X_m(N\text{—}R_7R_8)_n$
where
m represents an integer of two or more, and
each of $R_5$, $R_6$, $R_7$ and $R_8$ independently represents a hydrocarbon group which can be substituted with a substituent.

Two or more kinds of the organic compounds may be used.

Figure 9:
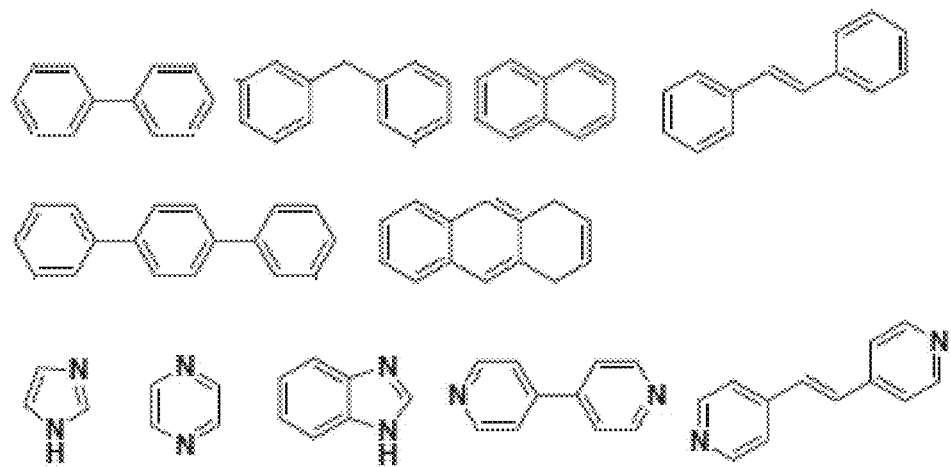
FIG. 9 is a drawing showing examples of the substituents $R_1$, $R_2$, $R_5$, and $R_6$.

FIG. 9 shows examples of $R_1$, $R_2$, $R_5$, and $R_6$. The hydrocarbon groups and the nitrogen-containing hydrocarbon groups shown in FIG. 9 can be substituted with a substituent.

When an electric field is applied to the porous metal-organic framework materials, note that the at least one organic compound must be a polar compound. This will be described later in more detail. For example, when an electric field is applied to the porous metal-organic framework materials, the at least one organic compound must not be a non-polar organic compound such as 1,3,5-benzene tricarboxylic acid.

See U.S. Pat. No. 8,115,024 for the porous metal-organic framework materials. U.S. Pat. No. 8,115,024 is incorporated herein by reference.

(2. Method for Adsorbing Carbon Dioxide)

First, a method for adsorbing carbon dioxide will be described. In the present specification, the method for adsorbing carbon dioxide is roughly divided into a method in an electric field and a method in a magnetic field.

(2.1 Method for Adsorbing Carbon Dioxide in an Electric Field)

A method for adsorbing carbon dioxide in an electric field will be described below.

As is described in more detail in the example A1, which will be described later, while an electric field or an electromagnetic field is applied to the porous metal-organic framework materials, the porous metal-organic framework materials is brought into contact with carbon dioxide to adsorb carbon dioxide onto the porous metal-organic framework materials. The electric field or the electromagnetic field applied to the porous metal-organic framework materials allows a larger amount of carbon dioxide to be adsorbed onto the porous metal-organic framework materials. In other words, compared to a case where no electric field or no electromagnetic field is applied to the porous metal-organic framework materials, when the porous metal-organic framework materials is brought into contact with carbon dioxide together with the application of the electric field or the electromagnetic field, the amount of carbon dioxide adsorbed onto the porous metal-organic framework materials is increased. It is desirable that an electric power supply and two electrodes are used to apply the electric field. It is desirable that the electric power supply is an alternating-current source. In other words, it is desirable that an alternating-electric field is applied to the porous metal-organic framework materials.

The porous metal-organic framework materials may be disposed between the two electrodes. Carbon dioxide is supplied to the porous metal-organic framework materials to be brought into contact with the porous metal-organic framework materials.

In the method for adsorbing carbon dioxide in an electric field, the organic compound must be a polar compound. As is demonstrated in the comparative example A1, which will be described later, in case where a non-polar compound is used, the amount of carbon dioxide adsorbed onto the porous metal-organic framework materials fails to be increased.

The term "non-polar compound" used in the present specification means an organic compound in which polarities of a plurality of functional groups contained in the non-polar compound are canceled in the compound. In other words, the "non-polar compound" means an organic compound in which the sum total of vectors of the polarities of the plurality of the functional groups each of which is capable of forming a coordination bond is zero. An example of the non-polar compound is 1,3,5-benzene tricarboxylic acid. On the other hand, an example of the polar compound is 1,3-benzene dicarboxylic acid.

On the other hand, in the method for adsorbing carbon dioxide in an electric field, the at least one metal ion is not limited. Not only $Cu^{2+}$ but also $Zn^{2+}$ may be used.

(2.2 Method for Adsorbing Carbon Dioxide in a Magnetic Field)

A method for adsorbing carbon dioxide in a magnetic field will be described below.

As is described in more detail in the example B1, which will be described later, while a magnetic field or an electromagnetic field is applied to the porous metal-organic framework materials, the porous metal-organic framework materials is brought into contact with carbon dioxide to adsorb carbon dioxide onto the porous metal-organic framework materials. The magnetic field or the electromagnetic field applied to the porous metal-organic framework materials allows a larger amount of carbon dioxide to be adsorbed onto the porous metal-organic framework materials. In other words, compared to a case where no magnetic field or no electromagnetic field is applied to the porous metal-organic framework materials, when the porous metal-organic framework materials are brought into contact with carbon dioxide together with the application of the magnetic field or the electromagnetic field, the amount of carbon dioxide adsorbed onto the porous metal-organic framework materials is increased. It is desirable that an electric power supply and a coil connected thereto are used to apply the magnetic field. It is desirable that the electric power supply is an alternating-current source. In other words, it is desirable that an alternating-magnetic field is applied to the porous metal-organic framework materials. The porous metal-organic framework materials may be disposed in the coil. Carbon dioxide is supplied to the porous metal-organic framework materials to be brought into contact with the porous metal-organic framework materials.

In the method for adsorbing carbon dioxide in a magnetic field, the at least one metal ion must have an unpaired electron. Since $Zn^{2+}$, $Cd^{2+}$, and $Hg^{2+}$ do not have an unpaired electron, $Zn^{2+}$, $Cd^{2+}$, and $Hg^{2+}$ must not be used in the method for adsorbing carbon dioxide in a magnetic field. In case where a metal ion which does not have an unpaired electron such as $Zn^{2+}$, $Cd^{2+}$, or $Hg^{2+}$ is used, the amount of carbon dioxide adsorbed onto the porous metal-organic framework materials fails to be increased.

On the other hand, in the method for adsorbing carbon dioxide in a magnetic field, the organic compound is not limited, as long as the organic compound has at least one functional group which is capable of forming at least two coordination bonds to the at least one metal ion. Not only a polar compound but also a non-polar compound may be used.

(3. Method for Cooling Porous Metal-Organic Framework Materials)

Next, a method for cooling porous metal-organic framework materials will be described. The method for cooling porous metal-organic framework materials is also divided into a method for cooling in an electric field and a method for cooling in a magnetic field.

Adsorbates are supplied to the porous metal-organic framework materials to impregnate the inside of the porous metal-organic framework materials with the adsorbates. It is desirable that gaseous adsorbates such as water vapor are supplied. In this way, the adsorbates are held in the porous metal-organic framework materials. In other words, the porous metal-organic framework materials contain the adsorbates in this way.

An example of the adsorbates is water, ammonia, hydrogen fluoride, alcohol, aldehyde, carboxylic acid, amine, amide, imide, fluorinated hydrocarbon, or chlorofluorocarbon.

(3.1 Method for Cooling Porous Metal-Organic Framework Materials in an Electric Field)

A method for cooling porous metal-organic framework materials in an electric field will be described below.

As is described in more detail in the example C1, which will be described later, an electric field or an electromagnetic field is applied to the porous metal-organic framework materials containing the adsorbates. This releases the adsorbates from the porous metal-organic framework materials. When the adsorbates are released from the porous metal-organic framework materials, the adsorbates draw heat from the porous metal-organic framework materials. In this way, the porous metal-organic framework materials are cooled. When the adsorbates are water, the drawn heat may be referred to as "vaporization heat". It is desirable that an electric power supply and two electrodes are used to apply the electric field. It is desirable that the electric power supply is an alternating-current source. In other words, it is desirable that an alternating-electric field is applied to the porous metal-organic framework materials. The porous metal-organic framework materials may be disposed between the two electrodes.

Similarly to the case of the method for adsorbing carbon dioxide in an electric field, also in the method for cooling the porous metal-organic framework materials in an electric field, the organic compound must be a polar compound. In case where a non-polar compound is used, the porous metal-organic framework materials fail to be cooled. On the other hand, in the method for cooling the porous metal-organic framework materials in an electric field, the at least one metal ion is not limited. Not only $Cu^{2+}$ but also $Zn^{2+}$ may be used.

(3.2 Method for Cooling Porous Metal-Organic Framework Materials in a Magnetic Field)

A method for cooling porous metal-organic framework materials in a magnetic field will be described below. As is described in more detail in the example D1, which will be described later, a magnetic field or an electromagnetic field is applied to the porous metal-organic framework materials containing the adsorbates. Similarly to the case of the method for cooling the porous metal-organic framework materials in an electric field, this application releases the adsorbates from the porous metal-organic framework materials to cool the porous metal-organic framework materials. It is desirable that an electric power supply and a coil connected thereto are used to apply the magnetic field. It is desirable that the electric power supply is an alternating-current source. In other words, it is desirable that an alternating-magnetic field is applied to the porous metal-organic framework materials. The porous metal-organic framework materials may be disposed in the coil.

Similarly to the case of the method for adsorbing carbon dioxide in a magnetic field, also in the method for cooling the porous metal-organic framework materials in a magnetic field, the at least one metal ion must have an unpaired electron. In case where $Zn^{2+}$, $Cd^{2+}$, or $Hg^{2+}$ is used, the porous metal-organic framework materials fail to be cooled. On the other hand, in the method for cooling the porous metal-organic framework materials in a magnetic field, the organic compound is not limited to a polar compound. A non-polar compound may also be used.

(4. Method for Obtaining Aldehyde Using Porous Metal-Organic Framework Materials)

A method for obtaining aldehyde using the porous metal-organic framework materials will be described. In the present specification, aldehyde is represented by the chemical formula R—CHO (where R represents hydrogen or a hydrocarbon group which can be substituted with a substituent). The method for obtaining aldehyde using the porous metal-organic framework materials is also roughly divided into a method in an electric field and a method in a magnetic field.

(4.1 Method for Obtaining Aldehyde Using Porous Metal-Organic Framework Materials in an Electric Field)

A method for obtaining aldehyde using the porous metal-organic framework materials in an electric field will be described below.

As is described in more detail in the example E1, which will be described later, while an electric field or an electromagnetic field is applied to the porous metal-organic framework materials, R—$CH_2OH$ is brought into contact with the porous metal-organic framework materials to oxidize at least a part of R—$CH_2OH$. In this way, R—CHO is obtained. It is desirable that an electric power supply and two electrodes are used to apply the electric field. It is desirable that the electric power supply is an alternating-current source. In other words, it is desirable that an alternating-electric field is applied to the porous metal-organic framework materials. The porous metal-organic framework materials may be disposed between the two electrodes.

Similarly to the case of the method for adsorbing carbon dioxide in an electric field, also in the method for obtaining aldehyde using porous metal-organic framework materials in an electric field, the organic compound must be a polar compound. In case where a non-polar compound is used, no aldehyde is obtained. On the other hand, in the method for obtaining aldehyde using porous metal-organic framework materials in an electric field, the at least one metal ion is not limited. Not only $Cu^{2+}$ but also $Zn^{2+}$ may be used.

(4.2 Method for Obtaining Aldehyde Using Porous Metal-Organic Framework Materials in a Magnetic Field)

A method for obtaining aldehyde using the porous metal-organic framework materials in a magnetic field will be described below.

As is described in more detail in the example F1, which will be described later, while a magnetic field or an electromagnetic field is applied to the porous metal-organic framework materials, R—$CH_2OH$ is brought into contact with the porous metal-organic framework materials to oxidize at least a part of R—$CH_2OH$. In this way, R—CHO is obtained. It is desirable that an electric power supply and a coil connected thereto are used to apply the magnetic field. It is desirable that the electric power supply is an alternating-current source. In other words, it is desirable that an alternating-magnetic field is applied to the porous metal-organic framework materials. The porous metal-organic framework materials may be disposed in the coil.

Similarly to the case of the method for adsorbing carbon dioxide in a magnetic field, also in the method for obtaining aldehyde using the porous metal-organic framework materials in a magnetic field, the at least one metal ion must have an unpaired electron. In case where $Zn^{2+}$, $Cd^{2+}$, or $Hg^{2+}$ is used, aldehyde fails to be obtained. On the other hand, in the method for obtaining aldehyde using the porous metal-organic framework materials in a magnetic field, the organic compound is not limited to a polar compound. A non-polar compound may also be used.

(5. Method for Warming Porous Metal-Organic Framework Materials)

Finally, a method for warming the porous metal-organic framework materials will be described. A method for warming the porous metal-organic framework materials is also roughly divided into a method in an electric field and a method in a magnetic field.

(5.1 Method for Warming Porous Metal-Organic Framework Materials in an Electric Field)

A method for warming the porous metal-organic framework materials in an electric field will be described below.

In the method for warming the porous metal-organic framework materials in an electric field, while no electric field or no electromagnetic field is applied to the porous metal-organic framework materials, the adsorbates are not adsorbed onto the porous metal-organic framework materials even if they exist. On the other hand, when an electric field or an electromagnetic field is applied to the porous metal-organic framework materials in the presence of the adsorbates, the adsorbates are adsorbed onto the porous metal-organic framework materials to generate adsorption heat. This adsorption heat warms the porous metal-organic framework materials. In this way, the porous metal organic materials are warmed. It is desirable that an electric power supply and two electrodes are used to apply the electric field. It is desirable that the electric power supply is an alternating-current source. In other words, it is desirable that an alternating-electric field is applied to the porous metal-organic framework materials. The porous metal-organic framework materials may be disposed between the two electrodes.

An example of the adsorbates used in this warming method is water, ammonia, hydrogen fluoride, alcohol, aldehyde, carboxylic acid, amine, amide, imide, fluorinated hydrocarbon, or chlorofluorocarbon.

Similarly to the case of the method for cooling the porous metal-organic framework materials in an electric field, also in the method for warming the porous metal-organic framework materials in an electric field, the organic compound must be a polar compound. In case where a non-polar compound is used, the porous metal-organic framework materials fail to be warmed. On the other hand, in the method for warming the porous metal-organic framework materials in an electric field, the at least one metal ion is not limited. Not only $Cu^{2+}$ but also $Zn^{2+}$ may be used. As just described, when an electric field or an electromagnetic filed is applied to the porous metal-organic framework materials in the presence of the adsorbates, the adsorbates are adsorbed onto the porous metal-organic framework materials.

(5.2 Method for Warming Porous Metal-Organic Framework Materials in a Magnetic Field)

A method for warming the porous metal-organic framework materials in a magnetic field will be described below. While no magnetic field or no electromagnetic field is applied to the porous metal-organic framework materials even if the adsorbates exist, the adsorbates are not adsorbed onto the porous metal-organic framework materials. On the other hand, when a magnetic field or an electromagnetic field is applied to the porous metal-organic framework materials in the presence of the adsorbates, the adsorbates are adsorbed onto the porous metal-organic framework materials to generate adsorption heat. This adsorption heat warms the porous metal-organic framework materials. It is desirable that an electric power supply and a coil connected thereto are used to apply the magnetic field. It is desirable that the electric power supply is an alternating-current source. In other words, it is desirable that an alternating-magnetic field is applied to the porous metal-organic framework materials. The porous metal-organic framework materials may be disposed in the coil.

Similarly to the case of the method for cooling the porous metal-organic framework materials in a magnetic field, also in the method for warming the porous metal-organic framework materials in a magnetic field, the at least one metal ion must have an unpaired electron. In case where $Zn^{2+}$, $Cd^{2+}$, or $Hg^{2+}$ is used, the porous metal-organic framework materials fail to be warmed. On the other hand, in the method for warming the porous metal-organic framework materials in a magnetic field, the organic compound is not limited to a polar compound. A non-polar compound may also be used. An example of the adsorbates used in this warming method is same as that used in the method for warming the porous metal-organic framework materials in an electric field. As just described, a magnetic field or an electromagnetic filed is applied to the porous metal-organic framework materials in the presence of the adsorbates, the adsorbates are adsorbed on the porous metal-organic framework materials.

EXAMPLES

The present invention will be described in more detail with reference to the following examples.

Example A1

Copper sulfate (II) pentahydrate (0.60 grams) and 1,3-benzene dicarboxylic acid (0.15 grams) were added in a mixed solvent of water (10 milliliters) and N,N-dimethylformamide (10 milliliters) to prepare a mixture. The mixture was supplied to a pressure vessel made of polytetrafluoroethylene (hereinafter, referred to as "PTFE"). The mixture was heated under a temperature of 105 degrees Celsius for 24 hours to give a precipitate. Then, the precipitate was filtered. The precipitate was dried under a temperature of 105 degrees Celsius for one hour. In this way, porous metal-organic framework materials were synthesized.

Figure 1:
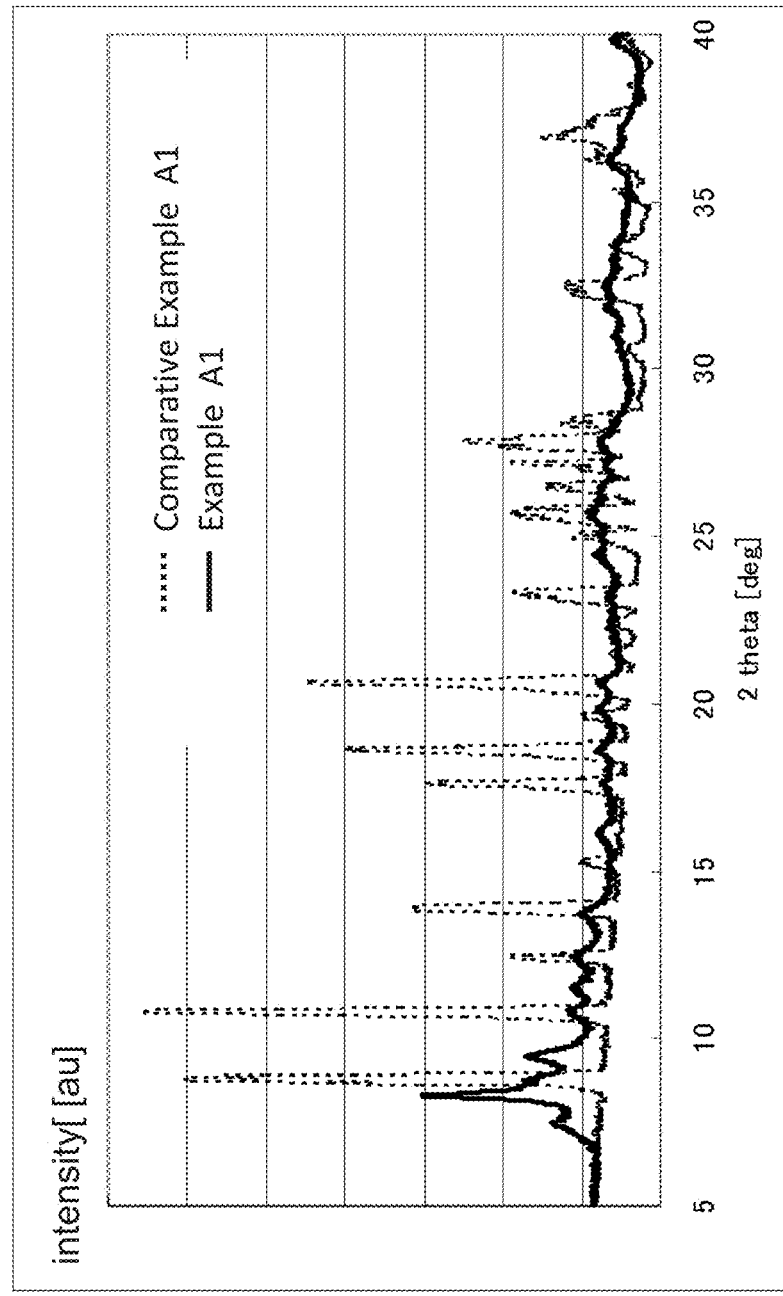
FIG. 1 is a graph indicating the X-ray diffraction results of the porous metal-organic framework materials obtained in the example A1.

The porous metal-organic framework materials were subjected to X-ray diffraction. FIG. 1 is a graph indicating the X-ray diffraction results of the synthesized porous metal-organic framework materials. FIG. 1 suggests that the crystal of the porous metal-organic framework materials was synthesized.

Figure 2:
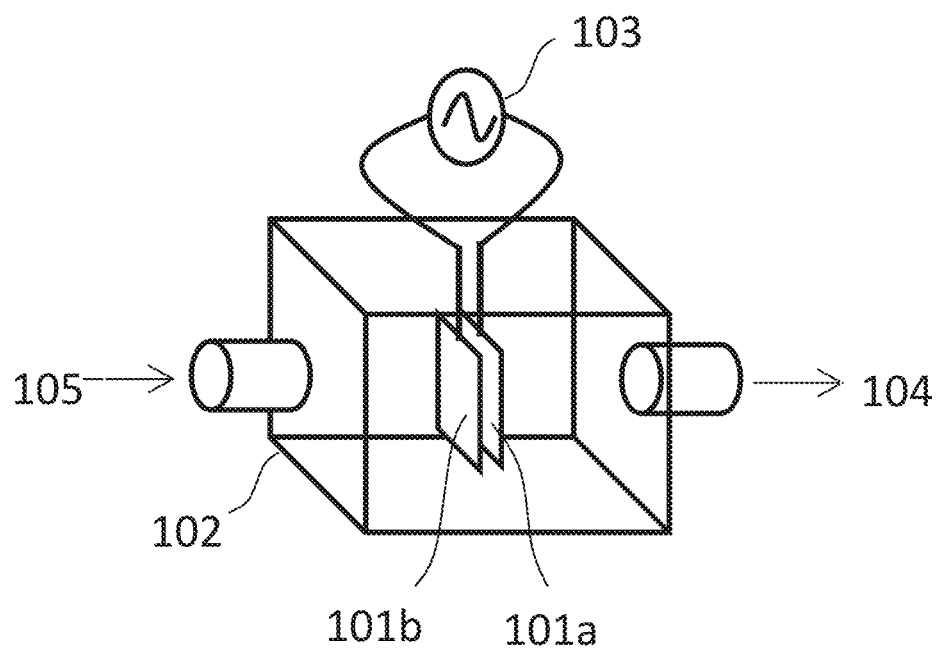
FIG. 2 shows a schematic view of a device for applying an electric field to the porous metal-organic framework materials.

Then, using a device shown in FIG. 2, adsorption properties of the porous metal-organic framework materials were observed. Hereinafter, the device shown in FIG. 2 will be briefly described. The device shown in FIG. 2 comprises a container 102, two electrodes 101, and an alternating-current source 103. Two electrodes 101 are composed of a first electrode 101a and a second electrode 101b. The porous metal-organic framework materials are disposed between the two electrodes 101. The alternating-current source 103 is used to generate an electric field between the two electrodes 101. The container 102 contains the two electrodes 101. The container 102 is provided with an inlet 105 and an outlet 104. A gas such as carbon dioxide is supplied to the container 102 from the inlet 105. The gas supplied to the container 102 is discharged from the outlet 104.

First, the synthesized porous metal-organic framework materials (0.2 grams) were sandwiched between the two electrodes 101. Each electrode 101 was a stainless-steel mesh electrode having a surface area of 1 cm$^2$. The container 102 had a capacity of 2 centimeters×2 centimeters×5 centimeters (20 milliliters).

Then, the inside of the container 102 was decompressed using a vacuum pump (not shown) connected through the outlet 104, until the inside of the container 102 had a pressure of not more than 1 Torr.

A gaseous mixture of hydrogen and carbon dioxide (volume ratio of $H_2/CO_2=3.7/1$) was supplied to the container 102 through the inlet 105, until the gaseous mixture had a pressure of 760 Torr. Hereinafter, the gaseous mixture supplied to the container 102 through the inlet 105 is referred to as a source gas. Subsequently, a part of the gaseous mixture contained in the container 102 was extracted. The extracted gaseous mixture was subjected to gas chromatography. As a result, the gas composition ratio ($H_2/CO_2$) of the gaseous mixture was 4.0. This value is the gas composition ratio of the gaseous mixture before an electric field was applied.

Then, the alternating-current source 103 was used to apply an AC voltage having a frequency of 60 Hz and a voltage of 1 volt between the two electrodes 101 for ten minutes. Subsequently, a part of the gaseous mixture contained in the container 102 was extracted again. The extracted gaseous mixture was subjected to gas chromatography. As a result of the gas chromatography, the gas composition ratio ($H_2/CO_2$) of the gaseous mixture was 4.3. This value is the gas composition ratio of the gaseous mixture after an electric field was applied.

Example A2

Figure 3:
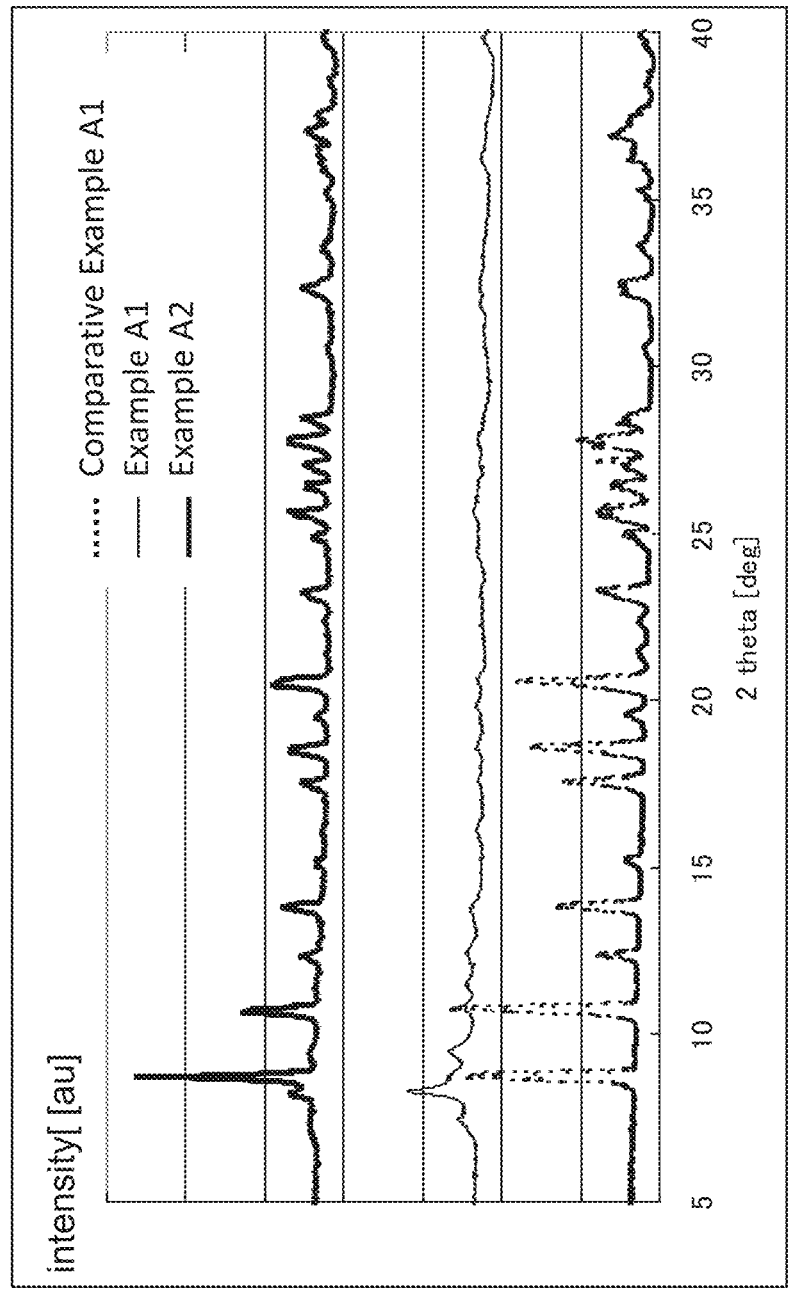
FIG. 3 is a graph indicating the X-ray diffraction results of the porous metal-organic framework materials obtained in the example A2.

An experiment similar to the example A1 was conducted, except that a mixture of 1,3-benzene dicarboxylic acid (0.03 grams) and 1,3,5-benzene tricarboxylic acid (0.12 grams) was used instead of 1,3-benzene dicarboxylic acid (0.15 grams). FIG. 3 is a graph indicating the X-ray diffraction results of the porous metal-organic framework materials obtained in the example A2.

Example A3

Figure 4:
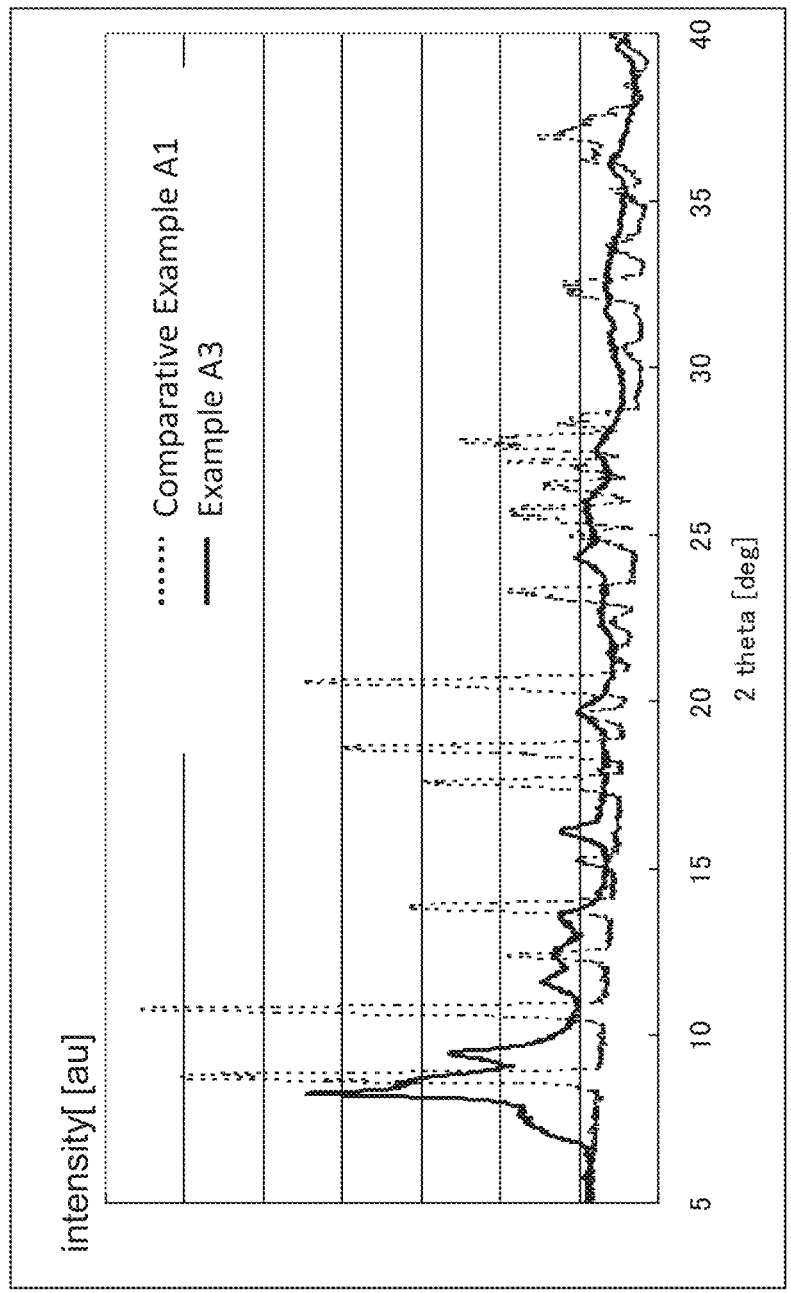
FIG. 4 is a graph indicating the X-ray diffraction results of the porous metal-organic framework materials obtained in the example A3.

An experiment similar to the example A1 was conducted, except that 1-cyano-3,5-benzene dicarboxylic acid (0.15 grams) was used instead of 1,3-benzene dicarboxylic acid (0.15 grams). FIG. 4 is a graph indicating the X-ray diffraction results of the porous metal-organic framework materials obtained in the example A3.

Example A4

Figure 5:
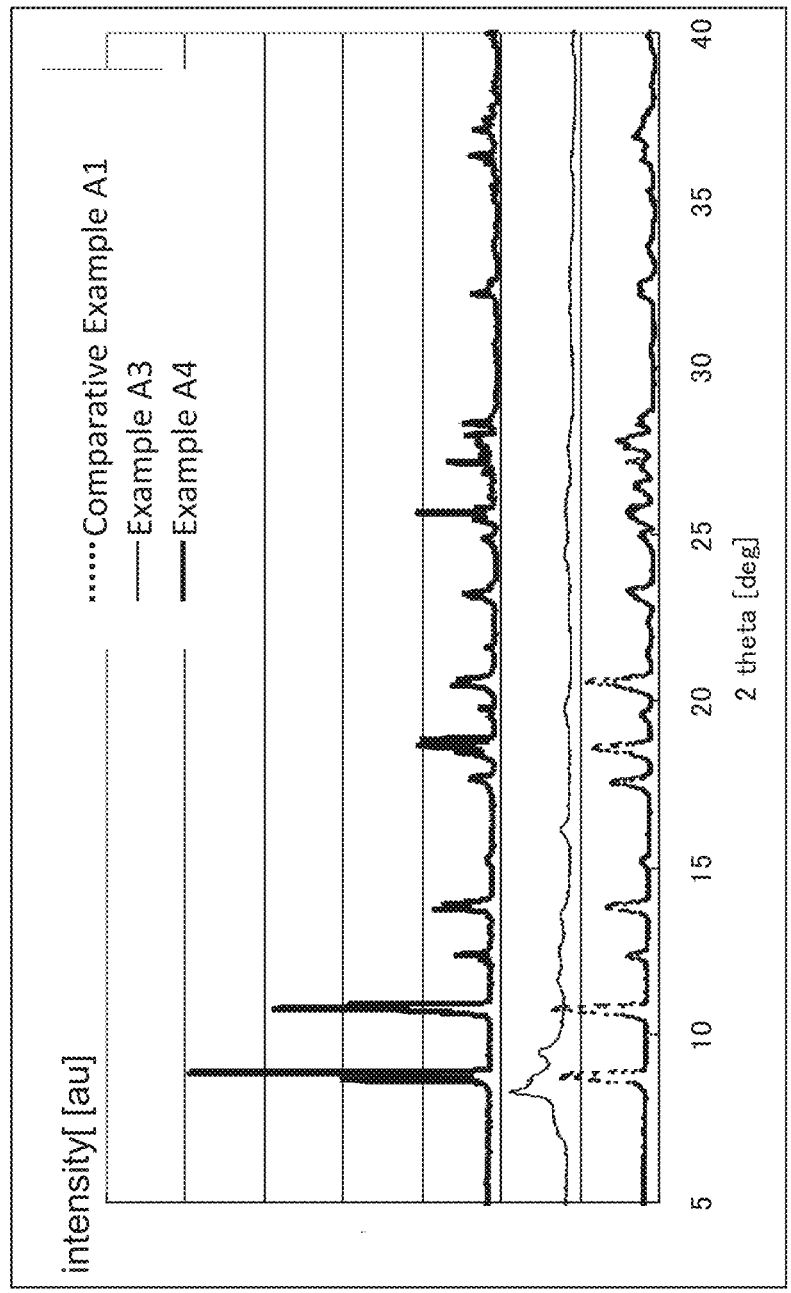
FIG. 5 is a graph indicating the X-ray diffraction results of the porous metal-organic framework materials obtained in the example A4.

An experiment similar to the example A1 was conducted, except that a mixture of 1-cyano-3,5-benzene dicarboxylic acid (0.03 grams) and 1,3,5-benzene tricarboxylic acid (0.12 grams) was used instead of 1,3-benzene dicarboxylic acid (0.15 grams). FIG. 5 is a graph indicating the X-ray diffraction results of the porous metal-organic framework materials obtained in the example A4.

Example A5

An experiment similar to the example A1 was conducted, except that 1-nitro-3,5-benzene dicarboxylic acid (0.15 grams) was used instead of 1,3-benzene dicarboxylic acid (0.15 grams).

Comparative example A1

Figure 6:
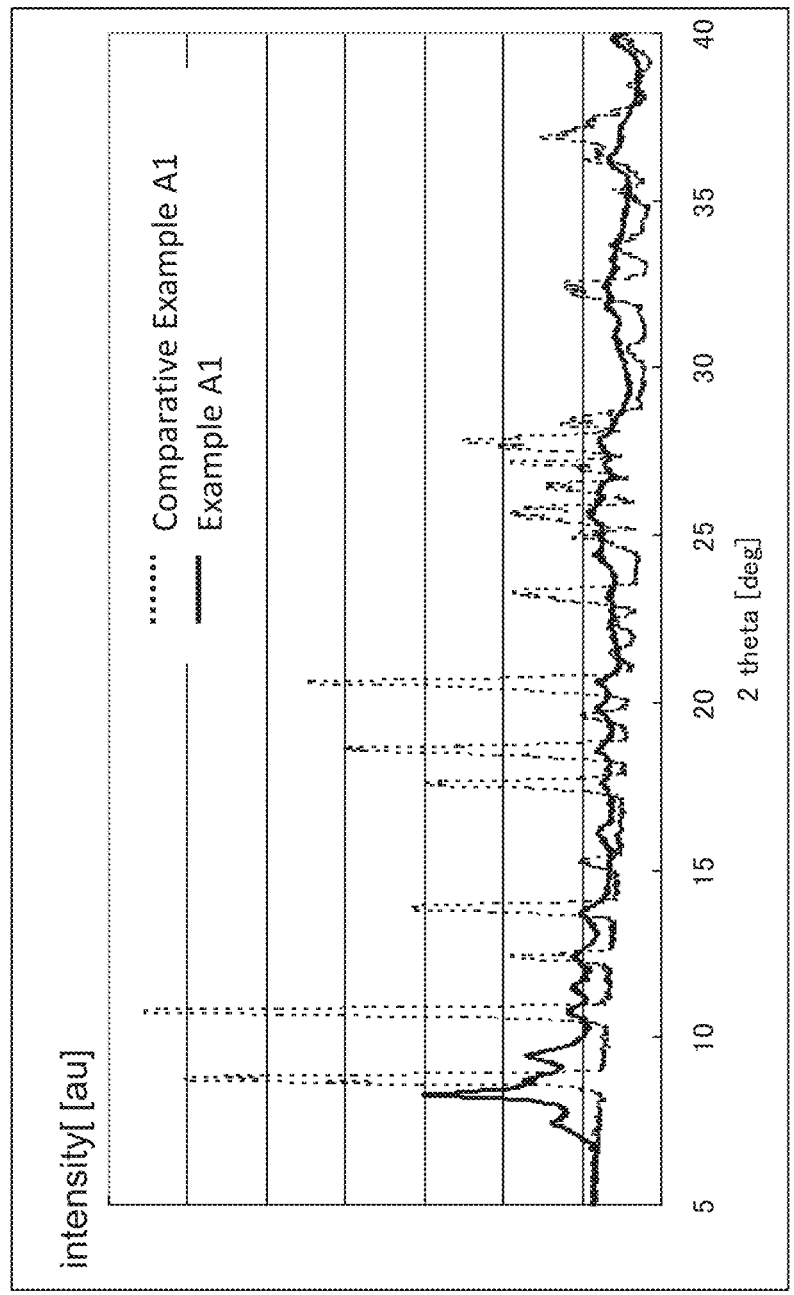
FIG. 6 is a graph indicating the X-ray diffraction results of the porous metal-organic framework materials obtained in the comparative example A1.

An experiment similar to the example A1 was conducted, except that 1,3,5-benzene tricarboxylic acid (0.15 grams) was used instead of 1,3-benzene dicarboxylic acid (0.15 grams). FIG. 6 is a graph indicating the X-ray diffraction results of the porous metal-organic framework materials obtained in the comparative example A1.

The following Table 1 shows the gas composition ratios of the gaseous mixtures which were measured before and after the electric fields were applied in the examples A1-A5 and the comparative example A1.

TABLE 1

|  | Gas composition ratio of the source gas | Gas composition ratio of the gaseous mixture before an electric field was applied | Gas composition ratio of gaseous mixture after an electric field was applied |
|---|---|---|---|
| Example A1 | 3.7 | 4.0 | 4.3 |
| Example A2 |  | 4.2 | 4.5 |
| Example A3 |  | 4.0 | 4.5 |
| Example A4 |  | 4.2 | 4.9 |
| Example A5 |  | 4.2 | 4.6 |
| Comparative example A1 |  | 4.2 | 4.2 |

As is clear from Table 1, except for the comparative example A1, the gas composition ratios of the gaseous mixtures after the electric fields were applied are higher than the gas composition ratios of the gaseous mixtures before the electric fields were applied. This reveals that the amount of carbon dioxide adsorbed onto the porous metal-organic framework materials is increased by bringing carbon dioxide into contact with the porous metal-organic framework materials under a condition where the electric field is applied to the porous metal-organic framework materials.

On the other hand, as seen in the comparative example A1, the amount of carbon dioxide adsorbed onto the porous metal-organic framework materials fails to be increased in case of using 1,3,5-benzene tricarboxylic acid, even when the electric field is applied to the porous metal-organic framework materials. This reveals that non-polar organic compounds such as 1,3,5-benzene tricarboxylic acid must not be used in the method for increasing the amount of carbon dioxide adsorbed onto the porous metal-organic framework materials in the electric field. In other words, a polar organic compound must be used.

Example B1

Similarly to the example A1, the porous metal-organic framework materials were synthesized.

Figure 7:
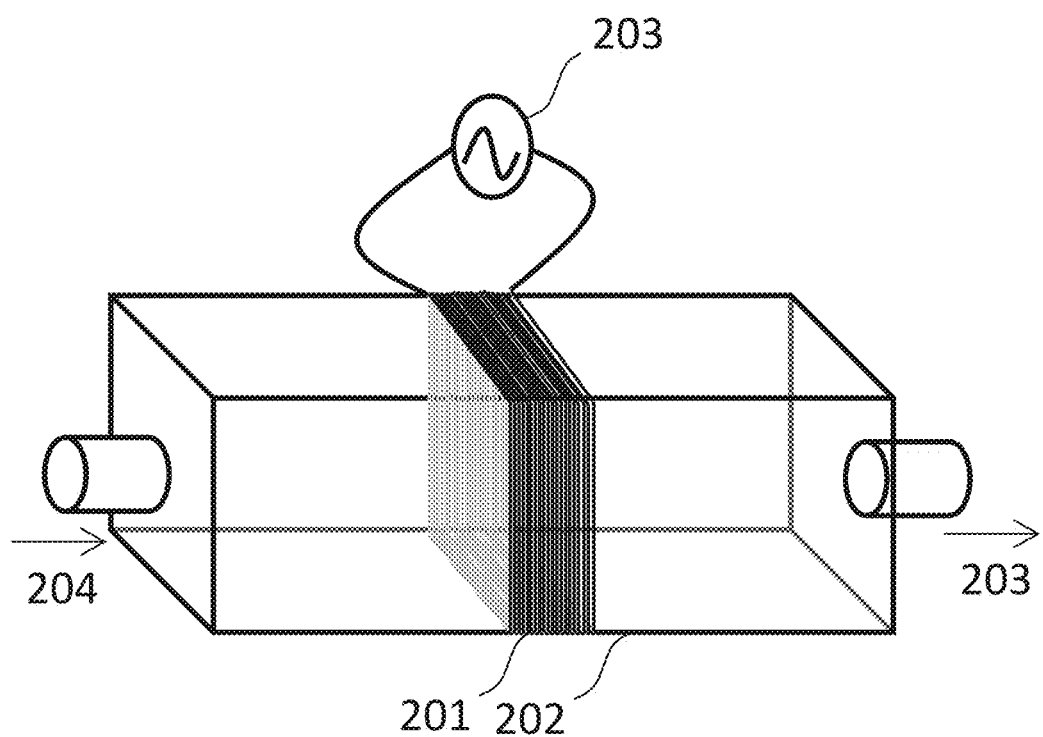
FIG. 7 shows a schematic view of a device for applying a magnetic field to the porous metal-organic framework materials.

Then, using a carbon dioxide adsorption device shown in FIG. 7, adsorption properties of the porous metal-organic framework materials were observed. Hereinafter, the carbon dioxide adsorption device shown in FIG. 7 will be briefly described. The carbon dioxide adsorption device shown in FIG. 7 comprises a container 202, a coil 201, and an alternating-current source 203. The coil 201 is wound around the container 202. The porous metal-organic framework materials are disposed in the center of the coil 201. A magnetic field is generated in the coil 201 using the alternating-current source 203 to apply a magnetic field to the porous metal-organic framework materials. The container 202 is provided with an inlet 205 and an outlet 204. A gas such as carbon dioxide is supplied to the container 202 from the inlet 205. The gas supplied to the container 202 is discharged from the outlet 204.

First, the synthesized porous metal-organic framework materials (0.2 grams) were disposed in the center of the coil 201. The coil 201 was provided by winding an enamel wire having a diameter of 0.5 mm twenty times around the container 202. The container 202 had a capacity of 1 centimeter×1 centimeter×10 centimeters (10 milliliters). The container 202 was formed of acrylic.

Then, the inside of the container 202 was decompressed using a vacuum pump (not shown) connected through the outlet 204, until the inside of the container 202 had a pressure of not more than 1 Torr.

A gaseous mixture of hydrogen and carbon dioxide (volume ratio of $H_2/CO_2=3.7/1$) was supplied to the container 202 through the inlet 205, until the gaseous mixture had a pressure of 760 Torr. Hereinafter, the gaseous mixture supplied to the container 202 through the inlet 205 is referred to as a source gas. Subsequently, a part of the gaseous mixture contained in the container 202 was extracted. The extracted gaseous mixture was subjected to gas chromatography. As a result of the gas chromatography, the gas composition ratio ($H_2/CO_2$) of the gaseous mixture was 4.2. This value is a gas composition ratio of the gaseous mixture before a magnetic field is applied.

Then, the alternating-current source 203 was used to apply an AC voltage having a frequency of 60 Hz and a voltage of 1 volt to the coil 201 for ten minutes. Subsequently, a part of the gaseous mixture contained in the container 202 was extracted again. The extracted gaseous mixture was subjected to gas chromatography. As a result, the gas composition ratio ($H_2/CO_2$) of the gaseous mixture was 4.4. This value is the gas composition ratio of the gaseous mixture after the electric field was applied.

Example B2

An experiment similar to the example B1 was conducted, except that a mixture of 1,3-benzene dicarboxylic acid (0.03 grams) and 1,3,5-benzene tricarboxylic acid (0.12 grams) was used instead of 1,3-benzene dicarboxylic acid (0.15 grams).

Comparative Example B1

Figure 8:
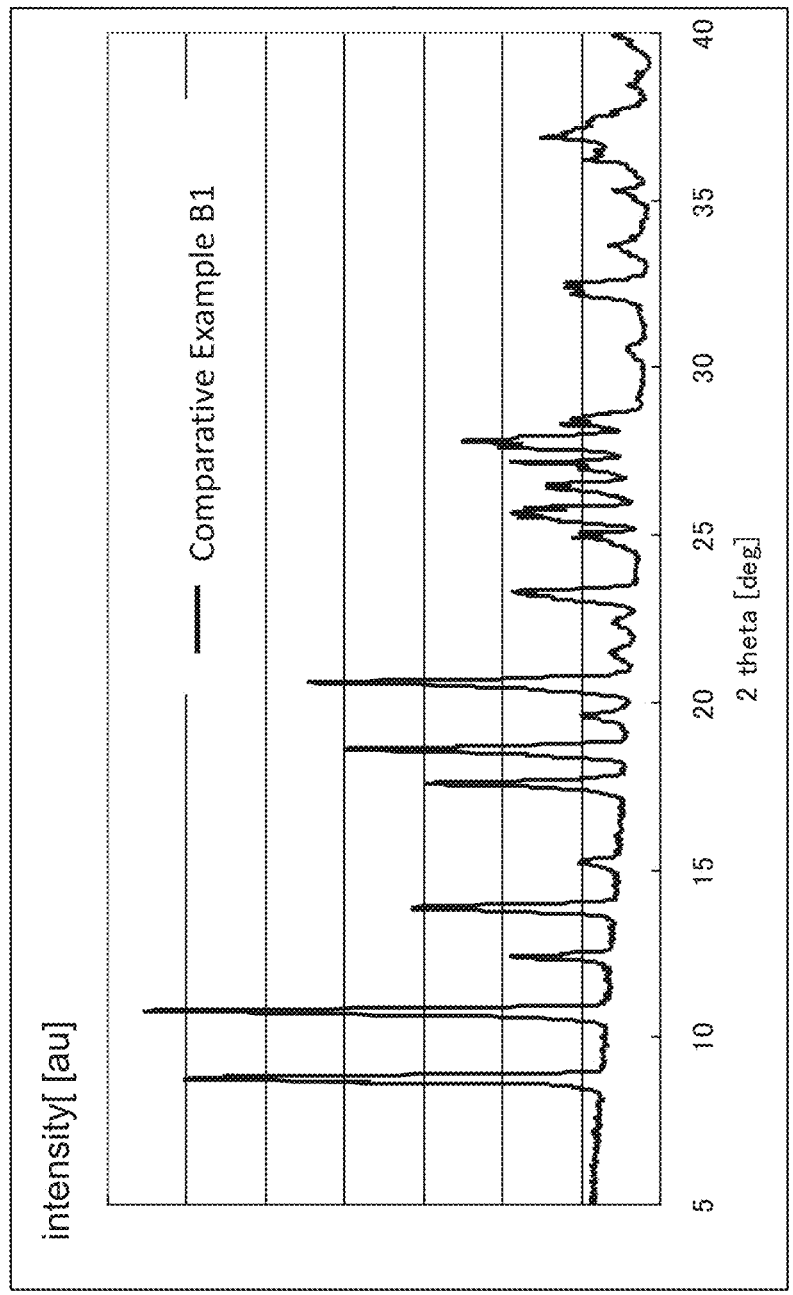
FIG. 8 is a graph indicating the X-ray diffraction results of the porous metal-organic framework materials obtained in the comparative example B1.

An experiment similar to the example B1 was conducted, except that zinc sulfate (II) pentahydrate (0.60 grams) was used instead of copper sulfate (II) pentahydrate (0.60 grams). FIG. 8 is a graph indicating the X-ray diffraction results of the porous metal-organic framework materials obtained in the comparative example B1.

The following Table 2 shows the gas composition ratios of the gaseous mixtures which were measured before and after the magnetic fields were applied in the examples B1-B2 and the comparative example B1.

TABLE 2

|  | Gas composition ratio of the source gas | Gas composition ratio of gaseous mixture before a magnetic field was applied | Gas composition ratio of gaseous mixture after a magnetic field was applied |
| --- | --- | --- | --- |
| Example B1 | 3.7 | 4.2 | 4.4 |
| Example B2 |  | 4.2 | 4.6 |
| Comparative example B1 |  | 4.2 | 4.2 |

As is clear from Table 2, except for the comparative example B1, the gas composition ratios of the gaseous mixtures after the magnetic fields were applied are higher than the gas composition ratios of the gaseous mixtures before the magnetic fields were applied. This reveals that the amount of carbon dioxide adsorbed onto the porous metal-organic framework materials is increased by bringing carbon dioxide into contact with the porous metal-organic framework materials under a condition where the magnetic field is applied to the porous metal-organic framework materials.

On the other hand, as seen in the comparative example B1, the amount of carbon dioxide adsorbed onto the porous metal-organic framework materials fails to be increased in case of using zinc ions, even when the magnetic field is applied to the porous metal-organic framework materials. This reveals that metal ions each of which does not have an unpaired electron, such as zinc ions, must not be used in the method for increasing the amount of carbon dioxide adsorbed onto the porous metal-organic framework materials in the magnetic field.

Example C1

Similarly to the example A3, porous metal-organic framework materials were synthesized. Similarly to the example A1, the synthesized porous metal-organic framework materials (0.2 grams) were interposed between the two electrodes 101 of the device shown in FIG. 2. The electrode 101a was provided with a thermometer composed of a thermocouple (not shown).

Then, the inside of the container 102 was decompressed using a vacuum pump (not shown) connected through the outlet 104 until the inside of the container 102 had a pressure of not more than 1 Torr. At this point, the porous metal-organic framework materials had a temperature of 19 degrees Celsius.

A nitrogen gas having an atmosphere temperature of 28 degrees Celsius and a humidity of 80% was supplied to the container 102 through the inlet 105 until the nitrogen gas had a pressure of 760 Torr. At this point, the temperature of the porous metal-organic framework materials was raised to 37 degrees Celsius. It was believed that this was because water was adsorbed onto the porous metal-organic framework materials as the adsorbates.

Then, the alternating-current source 103 was used to apply an AC voltage having a voltage of 1 volt and a frequency of 60 Hz between the two electrodes 101 for ten minutes. During the application of the AC voltage, the temperature of the porous metal-organic framework materials fell to 24 degrees Celsius. It was believed that this was because water contained as the adsorbates was released from the porous metal-organic framework materials by the action of the magnetic field. Finally, the application of the AC voltage was stopped. After the application of the AC voltage was stopped, the temperature of the porous metal-organic framework materials was raised to 33 degrees Celsius. It was believed that this was because water was adsorbed again onto the porous metal-organic framework materials as the adsorbates.

As is clear from the example C1, an electric field is applied to the porous metal-organic framework materials containing the adsorbates such as water to cool the porous metal-organic framework materials. From the viewpoint of the comparative example A1, it would be required to use a polar organic compound to cool the porous metal-organic framework materials in the electric field. As just described, an electric field or an electromagnetic field is applied to the porous metal-organic framework materials containing the adsorbates to release the adsorbates from the porous metal-organic framework materials.

Example D1

Similarly to the example A3, porous metal-organic framework materials were synthesized. Similarly to the example B1, the synthesized porous metal-organic framework materials (0.2 grams) were disposed in the center of the coil 201 of the device shown in FIG. 7. The coil 201 was provided with a thermometer composed of a thermocouple (not shown).

Then, the inside of the container 202 was decompressed using a vacuum pump (not shown) connected through the outlet 204 until the inside of the container 202 had a pressure of not more than 1 Torr. At this point, the porous metal-organic framework materials had a temperature of 25 degrees Celsius.

A nitrogen gas having an atmosphere temperature of 28 degrees Celsius and a humidity of 80% was supplied to the container 102 through the inlet 105 until the nitrogen gas had a pressure of 760 Torr. At this point, the temperature of the porous metal-organic framework materials was raised to 31 degrees Celsius. It was believed that this was because water was adsorbed onto the porous metal-organic framework materials as the adsorbates.

Then, the alternating-current source 103 was used to apply an AC voltage having a voltage of 1 volt and a frequency of 60 Hz to the coil 201 for ten minutes. During the application of the AC voltage, the temperature of the porous metal-organic framework materials fell to 26 degrees Celsius. It was believed that this was because water contained as the adsorbates was released from the porous metal-organic framework materials by the action of the magnetic field. Finally, the application of the AC voltage was stopped. After the application of the AC voltage was stopped, the temperature of the porous metal-organic framework materials was raised to 31 degrees Celsius. It was believed that this was because water was adsorbed again onto the porous metal-organic framework materials as the adsorbates.

As is clear from the example D1, a magnetic field is applied to the porous metal-organic framework materials containing the adsorbates such as water to cool the porous metal-organic framework materials. From the viewpoint of the comparative example B1, it would be required to use a metal ion having an unpaired electron to cool the porous metal-organic framework materials in the magnetic field. As just described, a magnetic field or an electromagnetic field is applied to the porous metal-organic framework materials containing the adsorbates to release the adsorbates from the porous metal-organic framework materials.

Example E1

Similarly to the example A3, porous metal-organic framework materials were synthesized. Similarly to the example A1, the synthesized porous metal-organic framework materials (0.2 grams) were interposed between the two electrodes 101 of the device shown in FIG. 2.

Then, the inside of the container 102 was decompressed using a vacuum pump (not shown) connected through the outlet 104 until the inside of the container 102 had a pressure of not more than 1 Torr.

Air having an atmosphere temperature of 28 degrees Celsius and an ethanol density of 10 ppm was supplied to the container 102 through the inlet 105 until the air had a pressure of 760 Torr. Subsequently, a part of the air contained in the container 102 was extracted. The extracted air was subjected to gas chromatography. As a result of the gas chromatography, the air extracted at this point contained no acetaldehyde.

Then, the alternating-current source 103 was used to apply an AC voltage having a voltage of 1 volt and a frequency of 60 Hz between the two electrodes 101 for ten minutes. Subsequently, a part of the air contained in the container 102 was extracted again. The extracted air was subjected to gas chromatography. As a result of the gas chromatography, the air extracted after the AC voltage had been applied contained acetaldehyde.

As is clear from the example E1, an electric field is applied to the porous metal-organic framework materials to use the porous metal-organic framework materials as a catalyst used to synthesize aldehyde from alcohol. From the viewpoint of the comparative example A1, it would be required to use a polar organic compound to obtain aldehyde in an electric field.

Example F1

Similarly to the example A3, porous metal-organic framework materials were synthesized. Similarly to the example B1, the synthesized porous metal-organic framework materials (0.2 grams) were disposed in the center of the coil 201 of the device shown in FIG. 7.

Then, the inside of the container 202 was decompressed using a vacuum pump (not shown) connected through the outlet 204 until the inside of the container 202 had a pressure of not more than 1 Torr.

Air having an atmosphere temperature of 28 degrees Celsius and an ethanol density of 10 ppm was supplied to the container 202 through the inlet 205 until the air had a pressure of 760 Torr. Subsequently, a part of the air contained in the container 202 was extracted. The extracted air was subjected to gas chromatography. As a result of the gas chromatography, the air extracted at this point contained no acetaldehyde.

Then, the power supply source 203 was used to apply an AC voltage having a voltage 1 volt and a frequency of 60 Hz to the coil 201 for ten minutes. Subsequently, a part of the air contained in the container 202 was extracted again. The extracted air was subjected to gas chromatography. As a result of the gas chromatography, the air extracted after the AC voltage had been applied contained acetaldehyde.

As is clear from the example F1, a magnetic field is applied to the porous metal-organic framework materials to use the porous metal-organic framework materials as a catalyst used to synthesize aldehyde from alcohol. From the viewpoint of the comparative example B1, it would be required to use a metal ion having an unpaired electron to obtain aldehyde in an electric field.

INDUSTRIAL APPLICABILITY

The present invention provides a method for adsorbing carbon dioxide onto porous metal-organic framework materials more effectively, a method for cooling porous metal-organic framework materials more effectively, a method for obtaining aldehyde using porous metal-organic framework materials and a method for warming porous metal-organic framework materials more effectively).

CONCLUSION (Inventions Derived from the Above Disclosure)

The inventions derived from the above disclosure are described below.

Item A1. A method for adsorbing carbon dioxide onto porous metal-organic framework materials, the method comprising:
(a) bringing carbon dioxide into contact with the porous metal-organic framework materials, while an electric field or an electromagnetic field is applied to the porous metal-organic framework materials, wherein
the porous metal-organic framework materials contain
at least one metal ion, and
at least one organic compound bound by coordination bond to the at least one metal ion; and
the at least one organic compound is a polar compound.

Item A2. The method according to Item A1, wherein
the electric field is an alternating-electric field.

Item A3. The method according to Item A1, wherein
the at least one metal ion is a copper ion.

Item A4. The method according to Item A1, wherein
the at least one organic compound is 1,3-benzene dicarboxylic acid.

Item B1. A method for adsorbing carbon dioxide onto porous metal-organic framework materials, the method comprising:
(a) bringing carbon dioxide into contact with the porous metal-organic framework materials, while a magnetic field or an electromagnetic field is applied to the porous metal-organic framework materials, wherein
the porous metal-organic framework materials contain
at least one metal ion, and
at least one organic compound bound by coordination bond to the at least one metal ion; and
the at least one metal ion has an unpaired electron.

Item B2. The method according to Item B1, wherein
the magnetic field is an alternating-magnetic field.

Item B3. The method according to Item B1, wherein
the at least one metal ion is a copper ion.

Item B4. The method according to Item B1, wherein
the at least one organic compound is 1,3,5-benzene tricarboxylic acid.

Item C1. A method for cooling porous metal-organic framework materials, the method comprising:
(a) applying an electric field or an electromagnetic field to the porous metal-organic framework materials containing an adsorbate such that the adsorbate is released from the porous metal-organic framework materials, wherein
the porous metal-organic framework materials contain
at least one metal ion, and
at least one organic compound bound by coordination bond to the at least one metal ion; and
the at least one organic compound is a polar compound.

Item C2. The method according to Item C1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.

Item C3. The method according to Item C1, wherein
the electric field is an alternating-electric field.

Item C4. The method according to Item C1, wherein
the at least one metal ion is a copper ion.

Item C5. The method according to Item C1, wherein
the at least one organic compound is 1,3-benzene dicarboxylic acid.

Item D1. A method for cooling porous metal-organic framework materials, the method comprising:
(a) applying a magnetic field or an electromagnetic field to the porous metal-organic framework materials containing an adsorbate such that the adsorbate is released from the porous metal-organic framework materials, wherein
the porous metal-organic framework materials contain
at least one metal ion, and
at least one organic compound bound by coordination bond to the at least one metal ion; and
the at least one metal ion has an unpaired electron.

Item D2. The method according to Item D1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.

Item D3. The method according to Item D1, wherein
the magnetic field is an alternating-magnetic field.

Item D4. The method according to Item D1, wherein
the at least one metal ion is a copper ion.

Item D5. The method according to Item D1, wherein
the at least one organic compound is 1,3,5-benzene tricarboxylic acid.

Item E1. A method for obtaining R—CHO (where R represents hydrogen or a hydrocarbon group which can be substituted with a substituent) using porous metal-organic framework materials, the method comprising:
(a) bringing R—$CH_2OH$ into contact with the porous metal-organic framework materials, while an electric field or an electromagnetic field is applied to the porous metal-organic framework materials, wherein
the porous metal-organic framework materials contain
at least one metal ion, and
at least one organic compound bound by coordination bond to the at least one metal ion; and
the at least one organic compound is a polar compound.

Item E2. The method according to Item E1, wherein
the electric field is an alternating-electric field.

Item E3. The method according to Item E1, wherein
the at least one metal ion is a copper ion.

Item E4. The method according to Item E1, wherein
the at least one organic compound is 1,3-benzene dicarboxylic acid.

Item E5. The method according to Item E1, wherein
R is $CH_3$.

Item F1. A method for obtaining R—CHO (where R represents hydrogen or a hydrocarbon group which can be substituted with a substituent) using porous metal-organic framework materials, the method comprising:
(a) bringing R—$CH_2OH$ into contact with the porous metal-organic framework materials, while a magnetic field or an electromagnetic field is applied to the porous metal-organic framework materials, wherein
the porous metal-organic framework materials contain
at least one metal ion, and
at least one organic compound bound by coordination bond to the at least one metal ion; and
the at least one metal ion has an unpaired electron.

Item F2. The method according to Item F1, wherein
the magnetic field is an alternating-magnetic field.

Item F3. The method according to Item F1, wherein
the at least one metal ion is a copper ion.

Item F4. The method according to Item F1, wherein
the at least one organic compound is 1,3,5-benzene tricarboxylic acid.
Item F5. The method according to Item F1, wherein
R is $CH_3$.
Item G1. A method for warming porous metal-organic framework materials, the method comprising:
(a) applying an electric field or an electromagnetic field to the porous metal-organic framework materials in the presence of an adsorbate such that the adsorbate is adsorbed onto the porous metal-organic framework materials, wherein
the porous metal-organic framework materials contain
at least one metal ion, and
at least one organic compound bound by coordination bond to the at least one metal ion; and
the at least one organic compound is a polar compound.
Item G2. The method according to Item G1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item G3. The method according to Item G1, wherein
the electric field is an alternating-electric field.
Item G4. The method according to Item G1, wherein
the at least one metal ion is a copper ion.
Item G5. The method according to Item G1, wherein
the at least one organic compound is 1,3-benzene dicarboxylic acid.
Item H1. A method for warming porous metal-organic framework materials, the method comprising:
(a) applying a magnetic field or an electromagnetic field to the porous metal-organic framework materials in the presence of an adsorbate such that the adsorbate is adsorbed onto the porous metal-organic framework materials, wherein
the porous metal-organic framework materials contain
at least one metal ion, and
at least one organic compound bound by coordination bond to the at least one metal ion; and
the at least one metal ion has an unpaired electron.
Item H2. The method according to Item H1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item H3. The method according to Item H1, wherein
the magnetic field is an alternating-magnetic field.
Item H4. The method according to Item H1, wherein
the at least one metal ion is a copper ion.
Item H5. The method according to Item H1, wherein
the at least one organic compound is 1,3,5-benzene tricarboxylic acid.
Item I1. A method for removing an adsorbate from porous metal-organic framework materials containing the adsorbate, the method comprising:
(a) applying an electric field or an electromagnetic field to the porous metal-organic framework materials containing the adsorbate such that the adsorbate is released from the porous metal-organic framework materials, wherein
the porous metal-organic framework materials contain
at least one metal ion, and
at least one organic compound bound by coordination bond to the at least one metal ion; and
the at least one organic compound is a polar compound.
Item I2. The method according to Item I1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item I3. The method according to Item I1, wherein
the electric field is an alternating-electric field.
Item I4. The method according to Item I1, wherein
the at least one metal ion is a copper ion.
Item I5. The method according to Item I1, wherein
the at least one organic compound is 1,3-benzene dicarboxylic acid.
Item J1. A method for removing an adsorbate from porous metal-organic framework materials containing the adsorbate, the method comprising:
(a) applying a magnetic field or an electromagnetic field to the porous metal-organic framework materials containing the adsorbate such that the adsorbate is released from the porous metal-organic framework materials, wherein
the porous metal-organic framework materials contain
at least one metal ion, and
at least one organic compound bound by coordination bond to the at least one metal ion; and
the at least one metal ion has an unpaired electron.
Item J2. The method according to Item J1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item J3. The method according to Item J1, wherein
the magnetic field is an alternating-magnetic field.
Item J4. The method according to Item J1, wherein
the at least one metal ion is a copper ion.
Item J5. The method according to Item J1, wherein
the at least one organic compound is 1,3,5-benzene tricarboxylic acid.
Item K1. A method for adsorbing an adsorbate onto porous metal-organic framework materials, the method comprising:
(a) applying an electric field or electromagnetic field to the porous metal-organic framework materials in the presence of the adsorbate such that the adsorbate is adsorbed onto the porous metal-organic framework materials, wherein
the porous metal-organic framework materials contain
at least one metal ion, and
at least one organic compound bound by coordination bond to the at least one metal ion; and
the at least one organic compound is a polar compound.
Item K2. The method according to Item K1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item K3. The method according to Item K1, wherein
the electric field is an alternating-electric field.
Item K4. The method according to Item K1, wherein
the at least one metal ion is a copper ion.
Item K5. The method according to Item K1, wherein
the at least one organic compound is 1,3-benzene dicarboxylic acid.
Item L1. A method for adsorbing an adsorbate onto porous metal-organic framework materials, the method comprising:
(a) applying a magnetic field or an electromagnetic field to the porous metal-organic framework materials in the presence of the adsorbate such that the adsorbate is adsorbed onto the porous metal-organic framework materials, wherein
  the porous metal-organic framework materials contain
    at least one metal ion, and
    at least one organic compound bound by coordination bond to the at least one metal ion; and
  the at least one metal ion has an unpaired electron.

Item L2. The method according to Item L1, wherein
  the adsorbate is selected from the group consisting of water, ammonia, hydrogen fluoride, alcohol, aldehyde, carboxylic acid, amine, amide, imide, fluorinated hydrocarbon and chlorofluorocarbon.

Item L3. The method according to Item L1, wherein
  the magnetic field is an alternating-magnetic field.

Item L4. The method according to Item L1, wherein
  the at least one metal ion is a copper ion.

Item L5. The method according to Item L1, wherein
  the at least one organic compound is 1,3,5-benzene tricarboxylic acid.

Item a1. A carbon dioxide adsorption device, comprising:
  porous metal-organic framework materials;
  two electrodes for interposing the porous metal-organic framework materials therebetween; and
  a power supply source for generating an electric field or an electromagnetic field between the two electrodes, wherein
  the porous metal-organic framework materials contain
    at least one metal ion, and
    at least one organic compound bound by coordination bond to the at least one metal ion;
  the at least one organic compound is a polar compound; and
  carbon dioxide is brought into contact with the porous metal-organic framework materials while the electric field or the electromagnetic field is applied to the porous metal-organic framework materials using the two electrodes and the power supply source.

Item a2. The device according to Item a1, wherein
  the electric field is an alternating-electric field.

Item a3. The device according to Item a1, wherein
  the at least one metal ion is a copper ion.

Item a4. The device according to Item a1, wherein
  the at least one organic compound is 1,3-benzene dicarboxylic acid.

Item b1. A carbon dioxide adsorption device, comprising:
  porous metal-organic framework materials;
  a coil in which the porous metal-organic framework materials are disposed; and
  a power supply source for generating a magnetic field or an electromagnetic field in the coil, wherein
  the porous metal-organic framework materials contain
    at least one metal ion, and
    at least one organic compound bound by coordination bond to the at least one metal ion;
  the at least one metal ion has an unpaired electron; and
  carbon dioxide is brought into contact with the porous metal-organic framework materials while the magnetic field or the electromagnetic field is applied to the porous metal-organic framework materials using the coil and the power supply source.

Item b2. The device according to Item b1, wherein
  the magnetic field is an alternating-magnetic field.

Item b3. The device according to Item b1, wherein
  the at least one metal ion is a copper ion.

Item b4. The device according to Item b1, wherein
  the at least one organic compound is 1,3,5-benzene tricarboxylic acid.

Item c1. A cooling device, comprising:
  porous metal-organic framework materials containing an adsorbate;
  two electrodes for interposing the porous metal-organic framework materials therebetween; and
  a power supply source for generating an electric field or an electromagnetic field between the two electrodes, wherein
  the porous metal-organic framework materials contain
    at least one metal ion, and
    at least one organic compound bound by coordination bond to the at least one metal ion;
  the at least one organic compound is a polar compound; and
  the adsorbate is released from the porous metal-organic framework materials by applying the electric field or the electromagnetic field to the porous metal-organic framework materials containing the adsorbate using the two electrodes and the power supply source.

Item c2. The device according to Item c1, wherein
  the adsorbate is selected from the group consisting of water, ammonia, hydrogen fluoride, alcohol, aldehyde, carboxylic acid, amine, amide, imide, fluorinated hydrocarbon and chlorofluorocarbon.

Item c3. The device according to Item c1, wherein
  the electric field is an alternating-electric field.

Item c4. The device according to Item c1, wherein
  the at least one metal ion is a copper ion.

Item c5. The device according to Item c1, wherein
  the at least one organic compound is 1,3-benzene dicarboxylic acid.

Item d1. A cooling device, comprising:
  porous metal-organic framework materials containing an adsorbate;
  a coil in which the porous metal-organic framework materials are disposed; and
  a power supply source for generating a magnetic field or an electromagnetic field in the coil, wherein
  the porous metal-organic framework materials contain
    at least one metal ion, and
    at least one organic compound bound by coordination bond to the at least one metal ion;
  the at least one metal ion has an unpaired electron; and
  the adsorbate is released from the porous metal-organic framework materials by applying the magnetic field or the electromagnetic field to the porous metal-organic framework materials containing the adsorbate using the coil and the power supply source.

Item d2. The device according to Item d1, wherein
  the adsorbate is selected from the group consisting of water, ammonia, hydrogen fluoride, alcohol, aldehyde, carboxylic acid, amine, amide, imide, fluorinated hydrocarbon and chlorofluorocarbon.

Item d3. The device according to Item d1, wherein
  the magnetic field is an alternating-magnetic field.

Item d4. The device according to Item d1, wherein
  the at least one metal ion is a copper ion.

Item d5. The device according to Item d1, wherein
  the at least one organic compound is 1,3,5-benzene tricarboxylic acid.

Item e1. A device for obtaining R—CHO (where R represents hydrogen or a hydrocarbon group which can be substituted with a substituent) from R—CH$_2$OH, the device comprising:
  porous metal-organic framework materials;
  two electrodes for interposing the porous metal-organic framework materials therebetween; and
  a power supply source for generating an electric field or an electromagnetic field between the two electrodes, wherein the porous metal-organic framework materials contain
at least one metal ion, and
at least one organic compound bound by coordination bond to the at least one metal ion;
the at least one organic compound is a polar compound; and
R—CH$_2$OH is brought into contact with the porous metal-organic framework materials to give R—CHO while the electric field or the electromagnetic field is applied to the porous metal-organic framework materials using the two electrodes and the power supply source.

Item e2. The device according to Item e1, wherein
the electric field is an alternating-electric field.

Item e3. The device according to Item e1, wherein
the at least one metal ion is a copper ion.

Item e4. The device according to Item e1, wherein
the at least one organic compound is 1,3-benzene dicarboxylic acid.

Item e5. The device according to Item e1, wherein
R is CH$_3$.

Item f1. A device for obtaining R—CHO (where R represents hydrogen or a hydrocarbon group which can be substituted with a substituent) from R—CH$_2$OH, the device comprising:
porous metal-organic framework materials;
a coil in which the porous metal-organic framework materials are disposed; and
a power supply source for generating a magnetic field or an electromagnetic field in the coil, wherein
the porous metal-organic framework materials contain
at least one metal ion, and
at least one organic compound bound by coordination bond to the at least one metal ion;
the at least one metal ion has an unpaired electron; and
R—CH$_2$OH is brought into contact with the porous metal-organic framework materials to give R—CHO while the magnetic field or the electromagnetic field is applied to the porous metal-organic framework materials using the coil and the power supply source.

Item f2. The device according to Item f1, wherein
the magnetic field is an alternating-magnetic field.

Item f3. The device according to Item f1, wherein
the at least one metal ion is a copper ion.

Item f4. The device according to Item f1, wherein
the at least one organic compound is 1,3,5-benzene tricarboxylic acid.

Item f5. The device according to Item f1, wherein
R is CH$_3$.

Item g1. A warming device, comprising:
porous metal-organic framework materials;
two electrodes for interposing the porous metal-organic framework materials therebetween; and
a power supply source for generating an electric field or an electromagnetic field between the two electrodes, wherein
the porous metal-organic framework materials contain
at least one metal ion, and
at least one organic compound bound by coordination bond to the at least one metal ion;
the at least one organic compound is a polar compound; and
an adsorbate is adsorbed onto the porous metal-organic framework materials by applying the electric field or the electromagnetic field to the porous metal-organic framework materials in the presence of the adsorbate using the two electrodes and the power supply source.

Item g2. The device according to Item g1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.

Item g3. The device according to Item g1, wherein
the electric field is an alternating-electric field.

Item g4. The device according to Item g1, wherein
the at least one metal ion is a copper ion.

Item g5. The device according to Item g1, wherein
the at least one organic compound is 1,3-benzene dicarboxylic acid.

Item h1. A warming device, comprising:
porous metal-organic framework materials;
a coil in which the porous metal-organic framework materials are disposed; and
a power supply source for generating a magnetic field or an electromagnetic field in the coil, wherein
the porous metal-organic framework materials contain
at least one metal ion, and
at least one organic compound bound by coordination bond to the at least one metal ion;
the at least one metal ion has an unpaired electron; and
an adsorbate is adsorbed onto the porous metal-organic framework materials by applying the magnetic field or the electromagnetic field to the porous metal-organic framework materials in the presence of the adsorbate using the coil and the power supply source.

Item h2. The device according to Item h1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.

Item h3. The device according to Item h1, wherein
the magnetic field is an alternating-magnetic field.

Item h4. The device according to Item h1, wherein
the at least one metal ion is a copper ion.

Item h5. The device according to Item h1, wherein
the at least one organic compound is 1,3,5-benzene tricarboxylic acid.

Item i1. A device for removing an adsorbate from porous metal-organic framework materials containing the adsorbate, the device comprising:
the porous metal-organic framework materials containing the adsorbate;
two electrodes for interposing the porous metal-organic framework materials therebetween; and
a power supply source for generating an electric field or an electromagnetic field between the two electrodes, wherein
the porous metal-organic framework materials contain
at least one metal ion, and
at least one organic compound bound by coordination bond to the at least one metal ion;
the at least one organic compound is a polar compound; and
the adsorbate is released from the porous metal-organic framework materials by applying the electric field or the electromagnetic field to the porous metal-organic framework materials containing the adsorbate using the two electrodes and the power supply source.

Item i2. The device according to Item i1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.

Item i3. The device according to Item i1, wherein
the electric field is an alternating-electric field.
Item i4. The device according to Item i1, wherein
the at least one metal ion is a copper ion.
Item i5. The device according to Item i1, wherein
the at least one organic compound is 1,3-benzene dicarboxylic acid.
Item j1. A device for removing an adsorbate from porous metal-organic framework materials containing the adsorbate, the device comprising:
the porous metal-organic framework materials containing the adsorbate;
a coil in which the porous metal-organic framework materials are disposed; and
a power supply source for generating a magnetic field or an electromagnetic field in the coil, wherein
the porous metal-organic framework materials contain
at least one metal ion, and
at least one organic compound bound by coordination bond to the at least one metal ion;
the at least one metal ion has an unpaired electron; and
the adsorbate is released from the porous metal-organic framework materials by applying the magnetic field or the electromagnetic field to the porous metal-organic framework materials containing the adsorbate using the coil and the power supply source.
Item j2. The device according to Item j1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item j3. The device according to Item j1, wherein
the magnetic field is an alternating-magnetic field.
Item j4. The device according to Item j1, wherein
the at least one metal ion is a copper ion.
Item j5. The device according to Item j1, wherein
the at least one organic compound is 1,3,5-benzene tricarboxylic acid.
Item k1. A device for adsorbing an adsorbate onto porous metal-organic framework materials, the device comprising:
the porous metal-organic framework materials;
two electrodes for interposing the porous metal-organic framework materials therebetween; and
a power supply source for generating an electric field or an electromagnetic field between the two electrodes, wherein
the porous metal-organic framework materials contain
at least one metal ion, and
at least one organic compound bound by coordination bond to the at least one metal ion;
the at least one organic compound is a polar compound; and
the adsorbate is adsorbed onto the porous metal-organic framework materials by applying the electric field or the electromagnetic field to the porous metal-organic framework materials in the presence of the adsorbate using the two electrodes and the power supply source.
Item k2. The device according to Item k1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item k3. The device according to Item k1, wherein
the electric field is an alternating-electric field.
Item k4. The device according to Item k1, wherein
the at least one metal ion is a copper ion.
Item k5. The device according to Item k1, wherein
the at least one organic compound is 1,3-benzene dicarboxylic acid.
Item l1. A device for adsorbing an adsorbate onto porous metal-organic framework materials, the device comprising:
the porous metal-organic framework materials;
a coil in which the porous metal-organic framework materials are disposed; and
a power supply source for generating a magnetic field or an electromagnetic field in the coil, wherein
the porous metal-organic framework materials contain
at least one metal ion, and
at least one organic compound bound by coordination bond to the at least one metal ion;
the at least one metal ion has an unpaired electron; and
the adsorbate is adsorbed onto the porous metal-organic framework materials by applying the magnetic field or the electromagnetic field to the porous metal-organic framework materials in the presence of the adsorbate using the coil and the power supply source.
Item l2. The device according to Item l1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
Item l3. The device according to Item l1, wherein
the magnetic field is an alternating-magnetic field.
Item l4. The device according to Item l1, wherein
the at least one metal ion is a copper ion.
Item l5. The device according to Item l1, wherein
the at least one organic compound is 1,3,5-benzene tricarboxylic acid.

REFERENTIAL SIGNS LIST

101 electrodes
101a first electrode
101b second electrode
102 container
103 power supply source
104 outlet
105 inlet
201 coil
202 container
203 power supply source
204 outlet
205 inlet

The invention claimed is:
1. A method for cooling porous metal-organic framework materials, the method comprising:
(a) applying an electric field or an electromagnetic field to the porous metal-organic framework materials containing an adsorbate such that the adsorbate is released from the porous metal-organic framework materials, wherein
the porous metal-organic framework materials contain
at least one metal ion, and
at least one organic compound bound by coordination bond to the at least one metal ion; and
the at least one organic compound is a polar compound.
2. The method according to claim 1, wherein
the adsorbate is selected from the group consisting of water, ammonia, hydrogen fluoride, alcohol, aldehyde, carboxylic acid, amine, amide, imide, fluorinated hydrocarbon and chlorofluorocarbon.
3. The method according to claim 1, wherein
the electric field is an alternating-electric field.

4. The method according to claim 1, wherein the at least one metal ion is a copper ion.

5. The method according to claim 1, wherein the at least one organic compound is 1,3-benzene dicarboxylic acid.

6. A method for cooling porous metal-organic framework materials, the method comprising:
(a) applying a magnetic field or an electromagnetic field to the porous metal-organic framework materials containing an adsorbate such that the adsorbate is released from the porous metal-organic framework materials, wherein
the porous metal-organic framework materials contain
at least one metal ion, and
at least one organic compound bound by coordination bond to the at least one metal ion; and
the at least one metal ion has an unpaired electron.

7. The method according to claim 6, wherein the adsorbate is selected from the group consisting of water, ammonia, hydrogen fluoride, alcohol, aldehyde, carboxylic acid, amine, amide, imide, fluorinated hydrocarbon and chlorofluorocarbon.

8. The method according to claim 6, wherein the magnetic field is an alternating-magnetic field.

9. The method according to claim 6, wherein the at least one metal ion is a copper ion.

10. The method according to claim 6, wherein the at least one organic compound is 1,3,5-benzene tricarboxylic acid.

11. A method for warming porous metal-organic framework materials, the method comprising:
(a) applying an electric field or an electromagnetic field to the porous metal-organic framework materials in the presence of an adsorbate such that the adsorbate is adsorbed onto the porous metal-organic framework materials, wherein
the porous metal-organic framework materials contain
at least one metal ion, and
at least one organic compound bound by coordination bond to the at least one metal ion; and
the at least one organic compound is a polar compound.

12. The method according to claim 11, wherein the adsorbate is selected from the group consisting of water, ammonia, hydrogen fluoride, alcohol, aldehyde, carboxylic acid, amine, amide, imide, fluorinated hydrocarbon and chlorofluorocarbon.

13. The method according to claim 11, wherein the electric field is an alternating-electric field.

14. The method according to claim 11, wherein the at least one metal ion is a copper ion.

15. The method according to claim 11, wherein the at least one organic compound is 1,3-benzene dicarboxylic acid.

16. A method for warming porous metal-organic framework materials, the method comprising:
(a) applying a magnetic field or an electromagnetic field to the porous metal-organic framework materials in the presence of an adsorbate such that the adsorbate is adsorbed onto the porous metal-organic framework materials, wherein
the porous metal-organic framework materials contain
at least one metal ion, and
at least one organic compound bound by coordination bond to the at least one metal ion; and
the at least one metal ion has an unpaired electron.

17. The method according to claim 16, wherein the adsorbate is selected from the group consisting of water, ammonia, hydrogen fluoride, alcohol, aldehyde, carboxylic acid, amine, amide, imide, fluorinated hydrocarbon and chlorofluorocarbon.

18. The method according to claim 16, wherein the magnetic field is an alternating-magnetic field.

19. The method according to claim 16, wherein the at least one metal ion is a copper ion.

20. The method according to claim 16, wherein the at least one organic compound is 1,3,5-benzene tricarboxylic acid.

21. A method for removing an adsorbate from porous metal-organic framework materials containing the adsorbate, the method comprising:
(a) applying an electric field or an electromagnetic field to the porous metal-organic framework materials containing the adsorbate such that the adsorbate is released from the porous metal-organic framework materials, wherein
the porous metal-organic framework materials contain
at least one metal ion, and
at least one organic compound bound by coordination bond to the at least one metal ion; and
the at least one organic compound is a polar compound.

22. The method according to claim 21, wherein the adsorbate is selected from the group consisting of water, ammonia, hydrogen fluoride, alcohol, aldehyde, carboxylic acid, amine, amide, imide, fluorinated hydrocarbon and chlorofluorocarbon.

23. The method according to claim 21, wherein the electric field is an alternating-electric field.

24. The method according to claim 21, wherein the at least one metal ion is a copper ion.

25. The method according to claim 21, wherein the at least one organic compound is 1,3-benzene dicarboxylic acid.

26. A method for removing an adsorbate from porous metal-organic framework materials containing the adsorbate, the method comprising:
(a) applying a magnetic field or an electromagnetic field to the porous metal-organic framework materials containing the adsorbate such that the adsorbate is released from the porous metal-organic framework materials, wherein
the porous metal-organic framework materials contain
at least one metal ion, and
at least one organic compound bound by coordination bond to the at least one metal ion; and
the at least one metal ion has an unpaired electron.

27. The method according to claim 26, wherein the adsorbate is selected from the group consisting of water, ammonia, hydrogen fluoride, alcohol, aldehyde, carboxylic acid, amine, amide, imide, fluorinated hydrocarbon and chlorofluorocarbon.

28. The method according to claim 26, wherein the magnetic field is an alternating-magnetic field.

29. The method according to claim 26, wherein the at least one metal ion is a copper ion.

30. The method according to claim 26, wherein the at least one organic compound is 1,3,5-benzene tricarboxylic acid.

* * * * *